(12) United States Patent
Gevaert et al.

(10) Patent No.: US 10,005,717 B2
(45) Date of Patent: Jun. 26, 2018

(54) PHOTO-REACTIVE BINDER

(71) Applicant: Allnex Belgium S.A., Drogenbos (BE)

(72) Inventors: Paul Gevaert, Geraardsbergen (BE); Steven Cappelle, Ninove (BE); Hugues Van Den Bergen, Drogenbos (BE); Ram Gupta, Stamford, CT (US)

(73) Assignee: ALLNEX BELGIUM S.A., Drogenbos (BE)

( * ) Notice: Subject to any disclaimer, the term of this patent is extended or adjusted under 35 U.S.C. 154(b) by 704 days.

(21) Appl. No.: 14/361,425

(22) PCT Filed: Dec. 18, 2012

(86) PCT No.: PCT/EP2012/076044
§ 371 (c)(1),
(2) Date: May 29, 2014

(87) PCT Pub. No.: WO2013/107588
PCT Pub. Date: Jul. 25, 2013

(65) Prior Publication Data
US 2014/0335326 A1 Nov. 13, 2014

(30) Foreign Application Priority Data
Jan. 20, 2012 (EP) ..................... 12151911

(51) Int. Cl.
| C07C 69/76 | (2006.01) |
| C07C 229/38 | (2006.01) |
| C07C 229/12 | (2006.01) |
| C09D 11/101 | (2014.01) |
| C09D 133/14 | (2006.01) |
| C07C 227/16 | (2006.01) |
| C09D 11/02 | (2014.01) |

(52) U.S. Cl.
CPC ............ C07C 229/38 (2013.01); C07C 69/76 (2013.01); C07C 227/16 (2013.01); C07C 229/12 (2013.01); C09D 11/02 (2013.01); C09D 11/101 (2013.01); C09D 133/14 (2013.01); *Y10T 428/24802* (2015.01)

(58) Field of Classification Search
CPC ..... C07C 69/76; C07C 227/16; C07C 229/12; C07C 229/38
See application file for complete search history.

(56) References Cited

U.S. PATENT DOCUMENTS

| 3,429,852 | A * | 2/1969 | Skoultchi | ................ | C08F 20/16 |
| | | | | | 522/154 |
| 4,022,674 | A | 5/1977 | Rosen | | |
| 4,134,814 | A | 1/1979 | Poortere et al. | | |
| 4,677,155 | A | 6/1987 | Finter | | |
| 4,797,347 | A | 1/1989 | Finter | | |
| 5,905,164 | A | 5/1999 | Anderson et al. | | |
| 8,530,510 | B2 * | 9/2013 | Loccufier | ................ | C07C 69/76 |
| | | | | | 514/434 |
| 8,536,217 | B2 * | 9/2013 | Loccufier | ................ | C08F 2/50 |
| | | | | | 514/434 |
| 2005/0037277 | A1 | 2/2005 | Herlihy et al. | | |
| 2006/0160915 | A1 * | 7/2006 | Fuchs | ................ | C08F 2/50 |
| | | | | | 522/6 |
| 2007/0243342 | A1 | 10/2007 | Shukla et al. | | |
| 2010/0227076 | A1 * | 9/2010 | Yokoi | ................ | C08F 2/50 |
| | | | | | 427/504 |
| 2011/0063388 | A1 | 3/2011 | Loccufier et al. | | |
| 2011/0159203 | A1 | 6/2011 | Loccufier et al. | | |
| 2011/0224324 | A1 | 9/2011 | Loccufier et al. | | |
| 2011/0282091 | A1 | 11/2011 | Liu et al. | | |
| 2014/0335326 | A1 | 11/2014 | Gevaert et al. | | |

FOREIGN PATENT DOCUMENTS

| CN | 1727320 | 2/2006 |
| CN | 102101896 A * | 6/2011 |
| CN | 102766045 | 11/2012 |
| CN | 103059168 | 4/2013 |
| CN | 104080865 | 10/2014 |
| EP | 2 130 817 | 12/2009 |
| EP | 2 161 290 | 3/2010 |
| EP | 2 199 273 | 6/2010 |
| EP | 2 617 705 | 7/2013 |
| EP | 2 617 783 | 7/2013 |

(Continued)

OTHER PUBLICATIONS

Machine translation of CN102101896 A acquired on Jun. 11, 2017.*

(Continued)

*Primary Examiner* — Gerard Higgins
(74) *Attorney, Agent, or Firm* — Wenderoth, Lind & Ponack, L.L.P.

(57) ABSTRACT

A compound obtained by reaction of one or more amines of general formula $NHR^6R^7$ with a benzophenone derivative of the following general formula (IX)

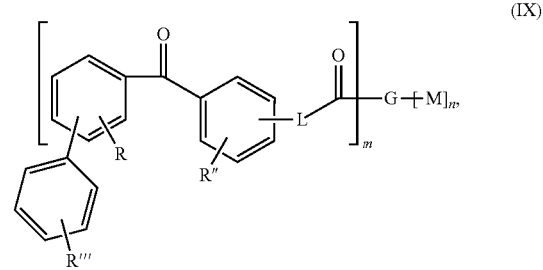

wherein
M is a group comprising a number z of (meth)acrylate groups equal to at least one,
L is a linker,
G is linker comprising a number p' of unreacted hydroxyl groups, and
R, R" and R'" are optional substituents
as well as inks, coating compositions and adhesives comprising the same.

9 Claims, No Drawings

(56) References Cited

FOREIGN PATENT DOCUMENTS

| | | |
|---|---|---|
| JP | S51-138730 | 11/1976 |
| JP | S58-103512 | 6/1983 |
| JP | H01-319504 | 12/1989 |
| JP | H06-263812 | 9/1994 |
| JP | H10-153855 | 6/1998 |
| JP | H10-161394 | 6/1998 |
| JP | 2000-503053 | 3/2000 |
| JP | 2004-061584 | 2/2004 |
| JP | 2015-509099 | 3/2015 |
| JP | 2015-511218 | 4/2015 |
| WO | 02/22700 | 3/2002 |
| WO | 03/033452 | 4/2003 |
| WO | 2009/147057 | 12/2009 |
| WO | 2010/029016 | 3/2010 |
| WO | 2010/029017 | 3/2010 |
| WO | 2010/069758 | 6/2010 |
| WO | 2011/117591 | 9/2011 |
| WO | 2012/136588 | 10/2012 |
| WO | 2012/136593 | 10/2012 |
| WO | 2013/107588 | 7/2013 |

OTHER PUBLICATIONS

Machine translation of JP 10-161394 acquired on Jun. 11, 2017.*

Lihua Hu et al., Synthesis and photoinitiating behavior of hyperbranched polymeric photoinitiators bearing coinitiator amine, Polymers Advanced Technologies, vol. 22, 2011, pp. 1673-1680.

Bishwa R. Nayak et al., Multifunctional Photo—for Acrylate and Methacrylate Polymerization, Polymer Preprints (American Chemical Society Division of Polymer Chemistry), vol. 46(1), 2005, pp. 700-701.

Carlo Carlini et al., Polymeric photoinitiators containing side chain benzophenone chromophores: Relationships between structure and activity, New Polymeric Materials, vol. 1, 1987, pp. 63-83.

Hyun-Sung Do et al., UV-curing behavior and adhesion performance of polymeric photoinitiators blended with hydrogenated rosin epoxy methacrylate for UV-crosslinkable acrylic pressure sensitive adhesives, European Polymer Journal, vol. 44, 2008, pp. 3871-3882.

Tymish Yu. Ogul'Chansky et al., Peculiarities of Triplet Exciton Jump Mechanism in Unconjugated Polymers with Pendant Benzophenone-Type Groups, Section A: Molecular Crystals and Liquid Crystals, vol. 361, 2001, pp. 25-30.

Luigi Angiolini et al., Copolymeric Systems Bearing Side-Chain Thioxanthone and a-Aminoacetophenone Moieties as Photoinitiators for Ultraviolet-Curable Pigmented Coatings, Journal of Applied Polymer Science, vol. 64, 1997, pp. 2247-2258.

Notification of the First Office Action dated Dec. 14, 2016 in Chinese Application No. 201380078382.3.

Yunxing et al., "Handbook of Ink Technology", Beijing: Printing Industry Publishing House, 1st Edition, pp. 887-888 (2009), with English Translation.

Allnex, "Radcure UV/EB Energy Curable Resins", Product Guide (2014).

International Search Report dated Feb. 26, 2013 in International (PCT) Application No. PCT/EP2012/076044.

Yang et al., "Highly Efficient Aza-Michael Reactions of Aromatic Amines and N-Heterocycles Catalyzed by a Basic Ionic Liquid under Solvent-Free Conditions", Tetrahedron Letters, vol. 47, pp. 7723-7726, 2006.

M. J. Bhanushali et al., "$Y(NO_3)_3 \cdot 6H_2O$ Catalyzed Aza-Michael Addition of Aromatic/Hetero-Aromatic Amines under Solvent-Free Conditions", Catalysis Communications, vol. 9, pp. 1189-1195, 2008.

International Search Report dated Nov. 26, 2013 in International (PCT) Application No. PCT/EP2013/065558.

International Search Report dated Feb. 26, 2013 in International (PCT) Application No. PCT/EP2012/076038.

* cited by examiner

PHOTO-REACTIVE BINDER

TECHNICAL FIELD OF THE INVENTION

The present invention relates to the field of photo-reactive binders for the preparation of inks, coatings and adhesives particularly suitable for the food industry.

BACKGROUND OF THE INVENTION

UV curable inks (flexo, offset, screen and inkjet) that are used for food packaging applications must fulfill very low migration level. Part of migration originates from the photoinitiator and from products of photo cleavage. Benzophenone is the most widely used photoinitiator for ultraviolet (UV) cured overprint varnishes as it has good surface curing, low yellowing and good solubility and is cheap and widely available. However, benzophenone is also known for its relatively strong odor and its ability to migrate and get extracted from print into foodstuffs, even through packaging such as board and plastic wrappers (see EP 1 438 282 B1). This has been partially solved by using "polymeric photoinitiators", i.e. photoinitiators with higher molecular weight. Most of the polymeric photoinitiators have solubility issues, poor reactivity and have a big impact on ink flow. When used in higher concentration to increase reactivity, they often act as plasticizer which is detrimental for the mechanical properties of the cured ink.

There is thus a need to develop photo-reactive binders with no or low migration level along with a high UV reactivity and low detrimental effect on ink flow and mechanical properties of the cured ink even when it is used in large concentration.

SUMMARY OF THE INVENTION

An object of the present invention is to provide a photo-reactive binder and more in particular a UV curable binder permitting the preparation of photo-reactive compositions showing good surface and deep curing while simultaneously having a very low migration level. This object has been realized by benzophenone derivatives according to the first and second aspect of the present invention.

In the first and second aspect of the present invention, the benzophenone derivatives may present one or more of the following advantages:
- they permit a good surface and deep curing,
- they may have a low yellowing,
- they may have a good solubility with other components of a UV formulation (e.g. with acrylates),
- they do not significantly act as plasticizers,
- they may be halogen-free.

In a further aspect of the present invention, the compositions (e.g. the inks, coating composition or adhesive) comprising the benzophenone derivatives of the present invention may present one or more of the following advantages:
- they can be used in food packaging due to their very low migration properties,
- they may have very good flow properties,
- they have high UV reactivity,
- they may have low yellowing,
- they may have weak or no odor,
- they may have good mechanical properties once cured (e.g. good scratch resistance).

The following terms are provided solely to aid in the understanding of the invention:

As used herein and unless otherwise stated, the term "$C_{1-n}$ alkyl" means straight, branched or cyclic (cycloalkyl) saturated hydrocarbon monovalent radicals having from 1 to n carbon atoms such as, for example, methyl, ethyl, propyl, n-butyl, 1-methylethyl (isopropyl), 2-methylpropyl(isobutyl), 1,1-dimethylethyl (ter-butyl), 2-methylbutyl, n-pentyl, dimethylpropyl, n-hexyl, cyclohexyl, 2-methylpentyl, 3-methylpentyl, n-heptyl and the like.

As used herein and unless otherwise stated, the term "$C_{2-n}$ alkenyl" designates straight, branched or cyclic hydrocarbon monovalent radicals having one or more ethylenic unsaturations and having from 2 to n carbon atoms such as, for example, vinyl, 1-propenyl, 2-propenyl(allyl), 1-butenyl, 2-butenyl, 2-pentenyl, 3-pentenyl, 3-methyl-2-butenyl, 3-hexenyl, 2-hexenyl, 2-heptenyl, 1,3-butadienyl, pentadienyl, hexadienyl, heptadienyl, heptatrienyl and the like, including all possible isomers thereof.

As used herein and unless otherwise stated, the term "$C_{1-n}$ alkylene" means the divalent hydrocarbon radical corresponding to the above defined $C_{1-n}$ alkyl.

As used herein with respect to a substituting radical, and unless otherwise stated, the term "aryl" designate any mono- or polycyclic aromatic monovalent hydrocarbon radical having from 6 up to 30 carbon atoms such as but not limited to phenyl, naphthyl, anthracenyl, phenantracyl, fluoranthenyl, chrysenyl, pyrenyl, biphenylyl, terphenyl, picenyl, indenyl, biphenyl, indacenyl, benzocyclobutenyl, benzocyclooctenyl and the like, including fused benzo-$C_{4-8}$ cycloalkyl radicals (the latter being as defined above) such as, for instance, indanyl, tetrahydronaphtyl, fluorenyl and the like.

As used herein and unless otherwise stated, the term "$C_{1-n}$ alkoxy" or "$C_{1-n}$ alkyloxy" is intended to include those $C_{1-n}$ alkyl groups of the designated length in either a linear or branched or cyclic configuration linked through an ether oxygen having its free valence bond from the ether oxygen. Examples of linear alkoxy groups are methoxy, ethoxy, propoxy, butoxy, pentoxy and hexoxy. Examples of branched alkoxy are isopropoxy, sec-butoxy, tert-butoxy, isopentoxy and isohexoxy. Example of cyclic alkoxy are cyclopropyloxy, cyclobutyloxy, cyclopentyloxy and cyclohexyloxy.

As used herein and unless otherwise stated, the term "$C_{1-n}$ alkoxy $C_{1-n}$ alkylene" refers to a $C_{1-n}$ alkylene as defined herein whereto is attached a $C_{1-n}$ alkoxy as defined herein, e.g. methoxymethyl, ethoxymethyl, methoxyethyl, ethoxyethyl, amongst others.

As used herein and unless otherwise stated, the term "(meth)acrylic" covers both "methacrylic" and "acrylic".

As used herein, the term "residue" when relating to a chemical compound, refers to the chemical structure remaining after that at least some of the reactive groups of the chemical compound have reacted. For instance, the term "residue of a polyhydroxy compound" refers to the chemical structure remaining after that at least some of the hydroxyl groups of the polyhydroxy compound have reacted (e.g. to form esters or urethanes).

In a first aspect, the present invention relates to a compound having the general formula (I),

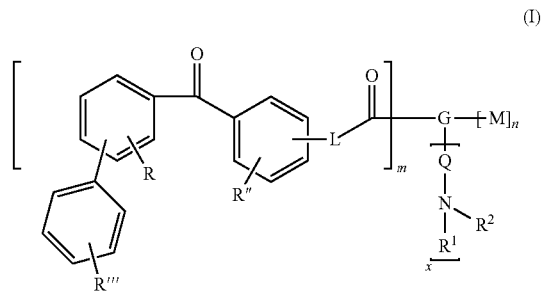

Wherein:
M is a group comprising a number z of (meth)acrylate groups equal to at least one,
L and Q are linkers, G is a linker comprising a number p of unreacted hydroxyl groups comprised between 0 and 100, $R^1$ and $R^2$ either:
  together with the N to which they are attached form a 5-6 membered saturated or aromatic ring optionally fused with a phenyl, said 5-6 membered ring containing one or more carbon atoms; from one to three nitrogen atom(s) and up to one oxygen atom, or
  are independently selected from the group consisting of
    H,
    $C_{1-30}$ alkyl,
    $C_{2-30}$ alkenyl, and
    5-6 membered saturated or aromatic ring containing one or more carbon atoms, up to three nitrogen atoms and up to two oxygen atoms, said ring being optionally substituted by a $C_{1-30}$ alkyl or by a $C_{1-30}$ alkyloxy or by a hydroxyl or by a $C_{1-6}$ alkyl substituted acyloxy or fused with a phenyl,
  wherein each of said $C_{1-30}$ alkyl and $C_{2-30}$ alkenyl (as $R^1$ or $R^2$ group or as a substituent on a $R^1$ or $R^2$ group being a 5-6 membered saturated or aromatic ring) are independently optionally substituted with one or more substituents independently selected from:
    a 5-6 membered saturated or aromatic ring containing one or more carbon atoms, up to three nitrogen atoms and up to two oxygen atoms,
    a hydroxyl group,
    a $C_{1-10}$ alkoxy group, and
    an amine of formula $—NR^3R^4$, wherein $R^3$ and $R^4$ are independently selected from the group consisting of H and $C_{1-8}$ alkyl, n is from 1 to 100,
m is from 1 to 100,
x is from 0 to 100, and
R, R" and R'" are independently selected from the group consisting of H, $C_{1-8}$ alkyl, $C_{1-10}$ alkoxy and halogen, with the proviso that if $R^1$ (or $R^2$) is a hydrogen atom, then the carbon atom in $R^2$ (or $R^1$) directly attached to the nitrogen (i.e. in alpha of the nitrogen) must be attached to at least two carbon atoms.

This compound is advantageously used in a coating (e.g. varnish), ink, or adhesive composition based on (meth)acrylics because it enables a very efficient curing of the (meth)acrylic composition while ensuring that few or no residual species prone to migration remains in the final product. The benzophenone type photoinitiator being of the type II, it does not lead to photocleavage products that can migrate upon curing. The photoinitiator being functionalized with at least one (meth)acrylic polymerizable function, it is incorporated in the poly(meth)acrylate network upon curing, thereby efficiently reducing or preventing migration. In the embodiments where x is not 0, the compound comprises its own co-initiator (an amine synergist) which is also covalently bound to the compound. This permits a very efficient curing even in presence of oxygen while assuring that few or no residual species prone to migration remains in the final product. This ability to avoid migration is particularly advantageous in compositions for use in inks or varnishes to be applied on food packaging. Without being bound by theory, it is believed that a faster intramolecular hydrogen transfer can be obtained when the benzophenone derivative and the amine synergist are bound together.

In an embodiment, z can be an integer from 1 up to 8. In general z is at most 3, often at most 2. In a particular embodiment z is 1.

In an embodiment, each one of the n M groups is independently selected from the list consisting of:

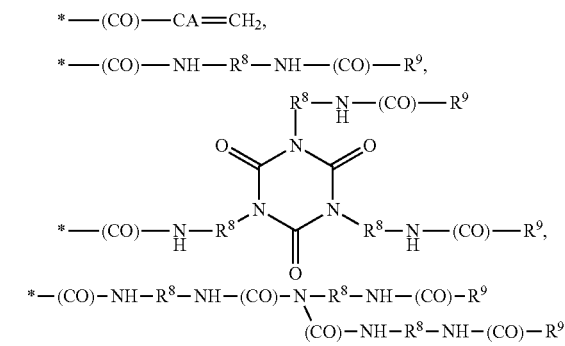

$R^9$ is a group comprising at least one (meth)acrylate group and the residue of a reactive group capable to react with an isocyanate,
$R^8$ is a divalent hydrocarbon group having from 1 to 20 carbon atoms (preferred examples infra), and
A is either H or $CH_3$.
The "*" indicates the point of attachment of the group to an oxygen atom on the linker G.

Embodiments where R, R" and R'" may be independently selected from the group consisting of H, $C_{1-8}$ alkyl and $C_{1-10}$ alkoxy are advantageous because of the absence of halogens. This is more environment-friendly and preferred for food packaging applications.

In an embodiment of the invention the group *—$NR^1R^2$ may originate from primary amines and/or secondary amines. Preferred in this category are often secondary amines though also a mix of one or more primary amines and one or more secondary amines may be used. Suitable primary amines you find further below (see the second aspect). Preferred in this category are monoethanolamine(2-aminoethanol), 2-ethylhexylamine, octylamine and/or cyclohexylamine and particularly preferred is octylamine. Examples of preferred secondary amines you find below. Particularly preferred in this category is di-butylamine.

In embodiments of the present invention, the molecular weight of the group *—$NR^1R^2$ is preferably of 30 g/mol or more, more preferably 36 g/mol or more and most preferably of 44 g/mol or more.

In embodiments of the present invention, the molecular weight of the group *—$NR^1R^2$ is preferably of 600 g/mol or less, more preferably 300 g/mol or less and most preferably of 250 g/mol or less.

In embodiments, $R^1$ and/or $R^2$ may be independently selected from alkyl and alkenyl groups independently comprising from 1 to 30 carbon atoms, preferably from 2 to 18 carbon atoms, optionally substituted by one or more hydroxyl groups.

In other embodiments, wherein $R^1$ or $R^2$ is an aromatic group, the group *—$NR^1R^2$ may originate from aromatic amines such as aniline, N-alkyl substituted aniline, isomers of aminophenol, (methylamino)phenol, ethyl-4-aminobenzoate and methyl-4-(methylamino)benzoate, and possibly mixtures thereof.

In embodiments, the group *—$NR^1R^2$ may originate from secondary amines such as diethylamine, diethanolamine, dipropylamine, dibutylamine, 2-(methylamino)ethanol, 2-methoxyethylamine, Bis(2-hydroxypropyl)amine, diisopropylamine, dipentylamine, dihexylamine, bis(2-ethylhexyl)amine, 1,2,3,4-Tetrahydroisoquino line, N-benzylmethylamine, diisopropylamine, morpholine, piperidine, dioctylamine, and di-cocoamine, and possibly mixtures thereof.

Preferred secondary amines are diethylamine, dipropylamine, dibutylamine, diethanolamine, dioctylamine, bis(2-ethylhexyl)amine, piperidine and morpholine. Most preferred are diethylamine, diethanolamine, dipropylamine, dibutylamine, dioctylamine and morpholine, and possibly mixtures thereof.

In other embodiments, wherein $R^1$ or $R^2$ is an aromatic group, the group *—$NR^1R^2$ may preferably originate from aromatic amines such as an optionally substituted aniline, optionally substituted N-alkylaniline, or an optionally substituted benzocaine (ethyl-4-amino benzoate).

In an embodiment, the group *—$NR^1R^2$ may be selected from the list consisting of *—$N((CH_2)_2CH_3)_2$, *—$N((CH_2)_3CH_3)_2$, *—$N((CH_2)_5CH_3)_2$,

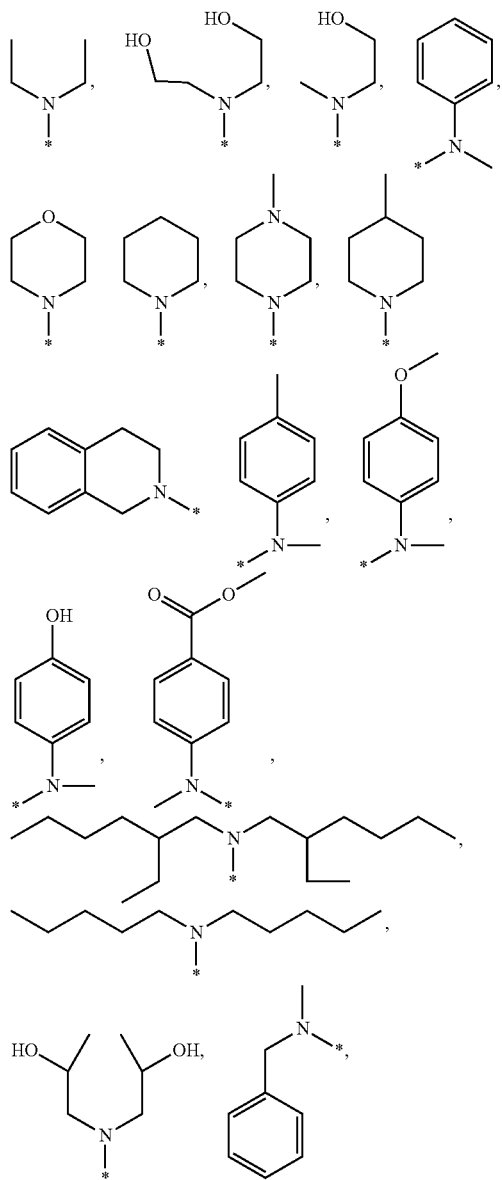

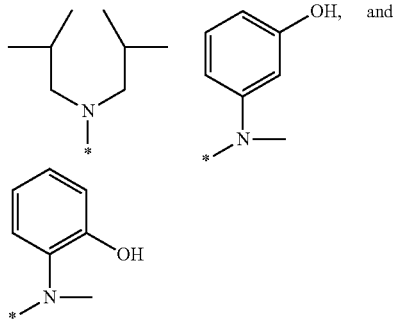

wherein "*" indicates the point of attachment of —$NR^1R^2$ to the linker Q.

Primary and secondary amines can add onto a meth(acrylic) reactive double bond via an Aza-Michael addition, permitting easy incorporation of one of the above amine synergists into a compound of the invention. By an "amine synergist" is meant to designate an amine capable of acting as an electron or hydrogen donor with a type II photoinitiator (also called a Norrish type II photoinitiator) like the one exemplified in the present invention. Type II photoinitiator systems can form an excited state upon irradiation, and then abstract an atom or electron from a donor molecule (synergist). The donor molecule then acts as the initiating species for polymerization. In the present invention the amine synergist is often also referred to as an "amine co-initiator".

Tertiary amines can be incorporated into a compound of the invention via e.g. a transesterification process. Examples of suitable compounds are dialkylaminobenzoate esters, like e.g. a 4-dimethylaminobenzoic acid ethyl ester and/or a 4-dimethylaminobenzoic acid methyl ester.

Polymeric tertiary amines can also be blended with the compounds of the invention. The polymeric tertiary amines used for that purpose according to this variant often comprise at least one aromatic group. By "polymeric" is meant that the number average molecular weight (Mn) of the polymeric tertiary amine is preferably of 400 g/mol or more, more preferably of 500 g/mol or more and most preferably of 600 g/mol or more. Typically the molecular weight of these compounds is at most 5.000 g/mol, more preferably at most 3.000 g/mol and most preferably at most 2.000 g/mol.

An example of suitable polymeric tertiary amines in this category: dialkyl aminobenzoate esters and more in particular dimethylaminobenzoate esters as described e.g. in U.S. Pat. No. 5,905,164. Both monoamines and diamines can be used, possibly a mixture of both.

An example of a suitable diamine compound in this category is polyethyleneglycol bis (p-dimethyl aminobenzoate) as disclosed in U.S. Pat. No. 5,905,164

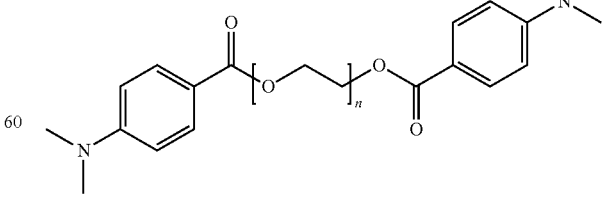

These compounds typically exist in a mixture as described in U.S. Pat. No. 5,905,164 p10, with n typically in the range of from 2 to 110, more preferably from 4 to 61, most preferably from 7 to 40.

Another example of a suitable diamine compound in this category is polytetrahydrofurane bis(p-dimethyl aminobenzoate)

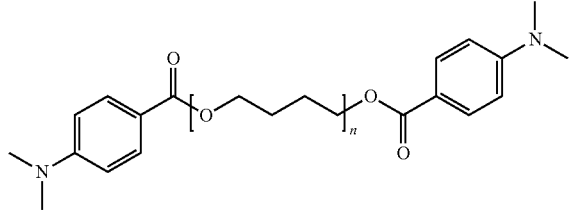

with n typically in the range of from 2 to 65, more preferably from 3 to 40, most preferably from 4 to 25.

An example of a suitable monoamine compound in this category is 4-N,N'-dimethylaminobenzoyl polyethyleneglycol monomethylether as disclosed in U.S. Pat. No. 5,905,164

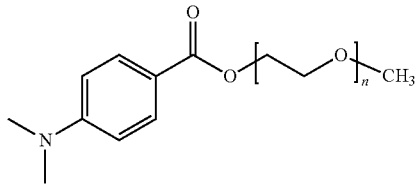

with n typically in the range of from 2 to 110, more preferably from 4 to 61, most preferably from 7 to 40.

Particularly preferred compounds in this category are Omnipol ASA from IGM (a to Poly(ethyleneglycol) bis(p-dimethylamino benzoate) with number average molecular weights 488-532 g/mol), ESACURE™ A198 from Lamberti & Speedcure 7040 from Lambson (polymeric (mix 4+2) amine with number average molecular weights 1060 g/mol).

In an embodiment of the first aspect, x may be 0. In this case, the compound according to the first aspect is preferably used together as a mixture with an amine-co initiator which may be added separately in the form of e.g. an amino (meth)acrylate, more in particular an aminoacrylate. One or more of the above described polymeric tertiary amines can also be used for that purpose. Possible a mixture of one or more amino (meth)acrylates and of one or more of these polymeric tertiary amines is being used. Other types of co-initiators that may be used in addition to or instead of the above include: aliphatic tertiary amines, aromatic amines and/or thiols.

Needless to say that said additional amine co-initiators can also be used in embodiments where x is not 0. In said variant of the invention the amine co-initiator increases the nitrogen content.

In an embodiment, L may be either a single bond, a group of general formula —O—Y— or a group of general formula -w-O(CO)-J- wherein Y and J are selected from the group consisting of $C_{1-3}$ alkylenes and $C_{1-3}$ alkoxy $C_{1-3}$ alkylenes, and wherein w is selected from the group consisting of $C_{1-3}$ alkylenes. Such a linker has the advantage to be synthetically readily accessible and to be stable under processing and curing conditions.

The phenyl bearing the R''' function may be attached to the benzophenone moiety in ortho, meta or para of its carbonyl function.

Preferably, the phenyl bearing the R''' function may be attached to the to benzophenone moiety in para of its carbonyl function.

Expressed differently, the compound of the first aspect may have the general formula (II)

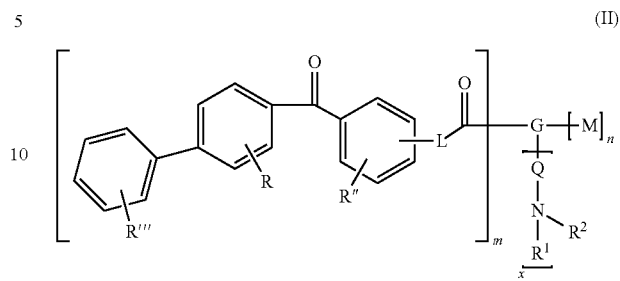

Having the R''' bearing phenyl in para of the carbonyl on the benzophenone has the advantage of a very rapid curing time both under air and under inert atmosphere.

The linker L may be attached at any position of the phenyl bearing the R'' function.

In a preferred embodiment, L may be a single bond. When L is a single bond, without being bound by theory it is believed that the distance between the benzophenone moiety and the optional amine synergist is minimal, favoring an efficient hydrogen transfer. Furthermore, the absence of the linker L (i.e. it is a single bond) limits to a minimum the dilution of the compound's properties, the increase of its viscosity and eventual adverse plasticizing effects.

In this embodiment, the compound may have the general formula (III)

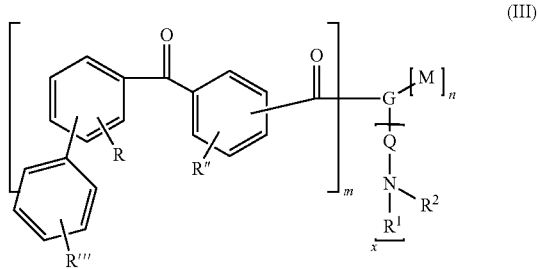

Preferably, the linker L when being a single bond may be attached in ortho of the carbonyl of the benzophenone moiety. For instance, when L is a single bond, the compound of the first aspect may have the general formula (IV)

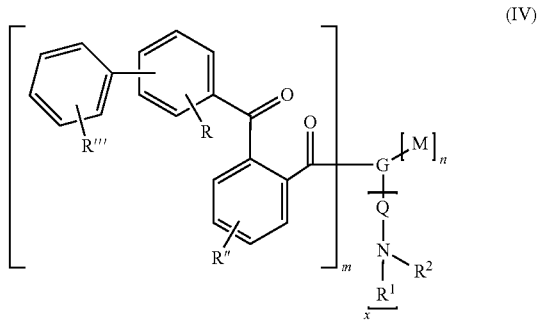

These embodiments where L is a single bond have the further advantage to be easily synthetically accessible from carboxy substituted benzophenone derivatives.

R, R'' and R''' may be at any position on their respective phenyl. R''' is however preferably in para of its attachment point to the benzophenone.

Still more preferred is the family of compounds (V)

Still more preferred is the family of compounds (V)

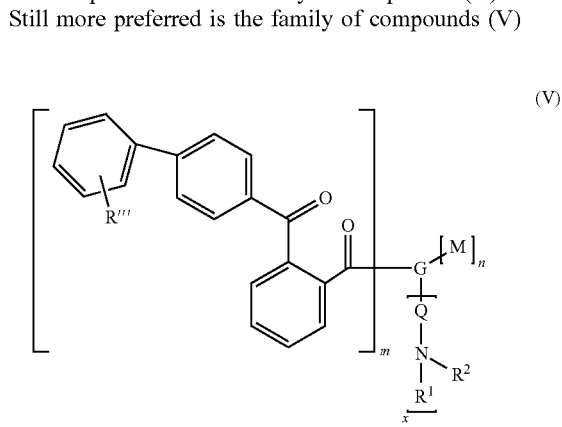

(V)

Still more preferred is the family of compounds having the general formula (VI)

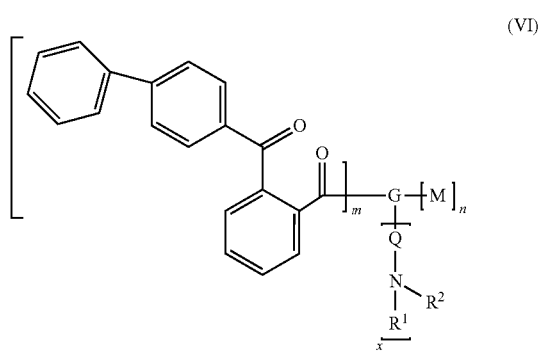

(VI)

In embodiments of the present invention, G may be a residue of a polyhydroxy compound having at least 2 hydroxyl groups, preferably at least 3 hydroxyl groups and most preferably at least 4 hydroxyl groups.

At least two hydroxyl groups permit the attachment of the linker to the benzophenone derivative on the one hand and to the M group (e.g. a (meth)acrylate) on the other hand. However, if x is not 0, at least three hydroxyl groups are needed in the polyhydroxy compound in order to permit the further attachment of the amine synergist (either via direct reaction on a hydroxyl group or via reaction on a (meth) acrylate). If x=0, at least three hydroxyl groups permit to attach at least two M groups to the linker. This in turn improves the chances of integration of the compound in a poly(meth)acrylate network after curing of a composition comprising the compound. If x=i, at least i+3 hydroxyl groups permit to attach at least two M groups to the linker. For instance, if x=1, at least four hydroxyl groups permit to attach at least two M groups to the linker. This in turn improves the chances of integration of the compound in a poly(meth)acrylate network after curing of a composition comprising the compound.

In embodiments, the polyhydroxy compound used to prepare the compound according to the first aspect may have at most 200 hydroxyl groups, preferably at most 150 hydroxyl groups, more preferably at most 100 hydroxyl groups, still more preferably at most 50 hydroxyl group, still more preferably at most 32 hydroxyl groups, still more preferably at most 16 hydroxyl groups, yet still more preferably at most 12 hydroxyl groups and most preferably at most 6 hydroxyl groups. A small number of hydroxyl groups lead to compounds having a relatively smaller molecular weight which is advantageous for having good solubility and low impact on the viscosity of compositions comprising it.

In embodiments, the polyhydroxy compound used to prepare the compound according to the first aspect can be selected from polyhydroxy derivatives of aliphatic or aromatic polyethers, polyhydroxy derivatives of polyesters, polyhydroxy derivatives of polyamides, polyhydroxy derivatives of polyimides, polyhydroxy derivatives of polycarbonates, styrene allyl alcohols copolymers (commercially available from Lyondell like SAA 100 or SAA 101), trimethylolpropane, di-trimethylolpropane, pentaerytritol, dipentaerytritol, hyperbranched or dendritic polyols, as well as C1-3 alkoxylated derivatives thereof (for instance oxypropylated and/or oxyethylated derivatives of any of the foregoing), and/or mixtures thereof.

In embodiments of the present invention, the polyhydroxy compound may have its hydroxyl groups modified into other reactive groups capable to react with a carboxylic acid or an activated carboxylic acid to form e.g. an ester. For instance, the polyhydroxy compound used to prepare the compound according to the first aspect may have some or all of its hydroxyl groups alkoxylated. The polyhydroxy compound may therefore have alkoxylated units, more preferably ethoxylated and/or propoxylated units.

The following alkoxylated polyhydroxy compounds are example of particularly suitable polyhydroxy compounds: Boltorn® H20; Boltorn® H2004; Boltorn® P1000; Boltorn® P500; polyol 3165, Polyol 3380, Polyol 4290; Polyol 4360; Polyol 4525; Polyol 4640, Polyol R3215, Polyol R3430; 6250 Polyol R4630; Polyol R4631; and 6430 Polyol R6405 from Perstorp.

In embodiments of the present invention, the polyhydroxy compound used to prepare the compound according to the first aspect may have a hydroxyl number between 100 and 1500 mg KOH/g, more preferably between 200 and 800 mg KOH/g, still more preferably between 200 and 600 mg KOH/g.

In embodiments of the present invention, the polyhydroxy compound used to prepare the compound according to the first aspect may have a number average molecular weight (Mn) between 100 and 5000 g/mol, more preferably between 300 and 3500 g/mol, still more preferably between 300 and 1300 g/mol.

The number average molecular weight of compounds is either calculated based on a target molecule representing the biggest fraction of the composition or measured by gel permeation chromatography (GPC) in case of higher molecular weight molecules. Therefore, a small portion of the oligomer is dissolved in tetrahydrofuran (THF) and injected in the liquid chromatograph after a preliminary filtration. The components of the sample are typically eluted by the mobile phase solvent (THF) at a flow rate of 1 ml/min and separated by a combination of polystyrene-divinylbenzene columns at a temperature of 40° C. Standards of polystyrene with known molecular weight and narrow polydispersity are used to generate a calibration curve.

Liquid polyhydroxy compounds are preferred as they may lead to liquid photo-reactive binders (which a.o. are more compatible and easy to handle and induce lower viscosity than solid photo-reactive binders).

The table below list examples of polyhydroxy compounds useful for use in the present invention:

|  | functionality | Hydroxy number mg KOH/g | Number average Molecular weight (g/mol) | Viscosity mPas, 23° C. |
|---|---|---|---|---|
| Polyol R2395 | 2 | 395 | 276 | 350 |
| Polyol R2490 | 2 | 490 | 220 | 170 |
| Polyol 3165 | 3 | 165 | 1014 | 350 |
| Polyol 3380 | 3 | 380 | 444 | 360 |
| Polyol 3610 | 3 | 610 | 275 | 700 |
| Polyol 3611 | 3 | 611 | 275 | 700 |
| Polyol 3940 | 3 | 940 | 179 | 4000 |
| Polyol 3990 | 3 | 990 | 170 | 4500 |
| Polyol R3215 | 3 | 215 | 795 | 340 |
| Polyol R3430 | 3 | 430 | 398 | 400 |
| Polyol R3530 | 3 | 530 | 308 | 2000 |
| Polyol R3540 | 3 | 540 | 311 | 550 |
| Polyol R3600 | 3 | 600 | 275 | 700 |
| Polyol 4290 | 4 | 290 | 797 | 450 |
| Polyol 4360 | 4 | 360 | 629 | 1300 |
| Polyol 4525 | 4 | 525 | 426 | 2600 |
| Polyol 4640 | 4 | 640 | 355 | 1100 |
| Polyol 4800 | 4 | 800 | 282 | 2200 |
| Polyol R4630 | 4 | 630 | 350 | 1500 |
| Polyol 4631 | 4 | 631 | 356 | 1500 |
| Polyol R6405 | 6 | 405 | 827 | 1900 |
| Boltorn P 1000 | — | 430-490 | — | 5000 |
| Boltorn P 500 | — | 560-630 | — | 15000 |
| Boltorn H 2004 |  | 105-125 | 3200 | 14000-20000 |
| Boltorn H 20 | 16 | 490-530 | 2100 | solid |
| PG17* | 17 | — | — | solid |
| PG33* | 33 | — | — | solid |
| PG83* | 83 | — | — | solid |
| PG179* | 179 | — | — | solid |

*a hyperbranched polyglycidol (available from HYPERPOLYMERS GMBH, Freiburg, Germany);

If x is not 0, Q may for instance be selected from the list consisting of a $C_{1-8}$ straight or branched alkylenoyl, a $C_{4-10}$ cyclic alkylenoyl optionally substituted with a $C_{1-4}$ straight or branched alkyl, and a phenylenoyl group optionally substituted with a $C_{1-4}$ straight or branched alkyl, wherein the carbonyl of Q forms an ester with a hydroxyl of the linker G. Preferably, Q equals to —C(O)(CHA-CH$_2$)— (as in formula VII). Most preferably A is a H atom.

In an embodiment, the compound may have the general formula (VII)

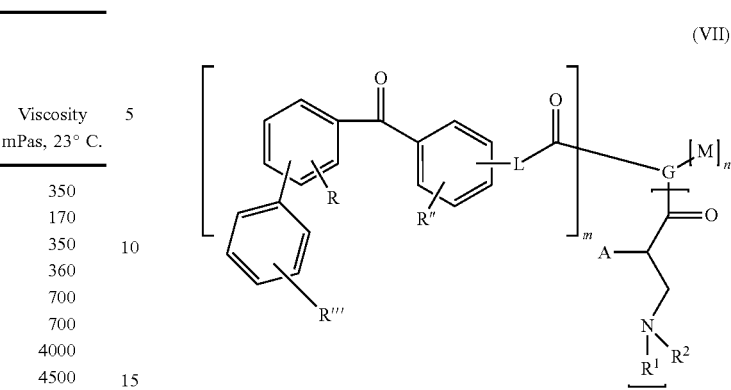

(VII)

Having Q equal to —C(O)(CHA-CH$_2$)—, with A preferably being an H atom, is advantageous as it is a short linker having therefore a minimal negative impact on the performance of the compound and of the compositions comprising it. Furthermore, it is a stable linker in the conditions of cure and processing. A further advantage of this linker is that it permits an easy incorporation of the amine synergist by Aza-Michael addition of at least one primary amine and/or at least one secondary amine onto a meth(acrylic) reactive double bond.

In embodiments of the present invention, A is preferably a H atom due to the higher reactivity of acrylates compared to methacrylates.

As an example, the compound may have the following formula (VIII)

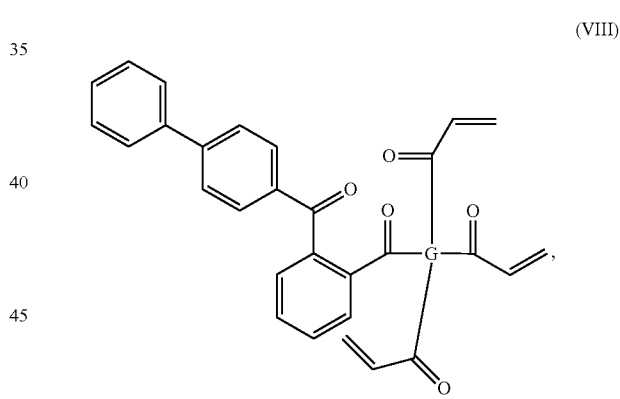

(VIII)

wherein G is a linker as defined above.

A typical example is depicted below wherein G is a di-trimethylolpropane residue and wherein x=0:

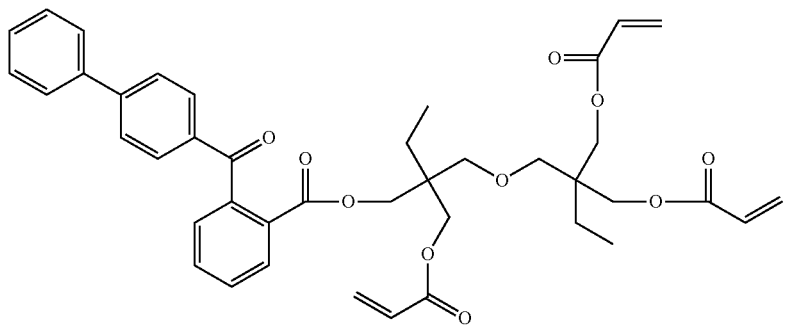 [SMILES: C=CC(=O)OCC(CC)(COCC(CC)(COC(=O)C=C)COC(=O)c1ccccc1C(=O)c1ccc(-c2ccccc2)cc1)COC(=O)C=C]

In an embodiment, the M group may be of the formula
*—(CO)—NH—R$^8$—NH—(CO)—R$^9$, In embodiments, the group *—(CO)NH—R$^8$—NH (CO)— in this formula may be the residue of a reacted diisocyanate.

In embodiments, R$^8$ may be a divalent hydrocarbon group having from 1 to 20 carbon atoms selected from the list consisting of:
- alkylenes (e.g. hexamethylene obtainable from hexamethylene diisocyanate),
- cycloalkylenes optionally substituted by one or more alkyl groups (e.g. cyclohexylene obtainable from cyclohexylene diisocyanate),
- arylenes (e.g. tolylene, a divalent tolidine radical or naphthylene each obtainable from their respective diisocyanate derivative), and
- Combinations thereof (such as alkylene cycloalkylene (e.g. divalent isophorone radical obtainable from reaction of isophorone diisocyante), alkylene arylene alkylene (e.g. xylylene obtainable from xylylene diisocyanate), alkylene cycloalkylene alkylene (e.g. hydrogenated xylylene obtainable from hydrogenated xylylene diisocyanate), cycloalkylene alkylene cycloalkylene (e.g. cyclohexylene methylene cyclohexylene obtainable from dicyclohexylmethane diisocyanate), arylene alkylene arylene (e.g. phenylene methylene phenylene obtainable from reaction of diphenylmethane diisocyanate), amongst others.)

In an embodiment, —R$^9$ may be a residue of a meth (acrylating) compound of a first type.

(Meth)acrylating compounds of said first type are compounds that contain at least one reactive group capable to react with isocyanate groups and that contain at least one (meth)acryloyl group. Typically (meth)acrylating compounds of said first type are end-capping agents that contain at least one acryloyl and/or methacryloyl group and one (or essentially one) nucleophilic function capable of reacting with isocyanate groups, such as a hydroxyl group. Useful (meth)acrylating compounds of said first type include the esterification products of aliphatic and/or aromatic polyols with (meth)acrylic acid having a residual average hydroxyl functionality of about 1. The partial esterification products of (meth)acrylic acid with tri-, tetra-, penta- or hexahydric polyols or mixtures thereof are preferred. In this context, it is also possible to use reaction products of such polyols with ethylene oxide and/or propylene oxide. These modified or unmodified polyols are partly esterified with acrylic acid, methacrylic acid or mixtures thereof until the desired residual hydroxyl functionality is reached. (Meth)acrylating compounds of said first type obtained from the reaction of (meth)acrylic acid with aliphatic, cycloaliphatic or aromatic compounds bearing an epoxy functionality together with at least one (meth)acrylic functionality can be used as well. Other suitable (meth)acrylating compounds of said first type are the (meth)acrylic esters with linear and branched polyols in which at least one hydroxy functionality remains free, like hydroxyalkyl(meth)acrylates having 1 to 20 carbon atoms in the alkyl group. Preferred molecules in this category are hydroxymethyl(meth)acrylate, hydroxyethyl (meth)acrylate, hydroxypropyl (meth)acrylate and/or hydroxybutyl (meth) acrylate. Preferred examples of poly(meth)acryloyl hydroxylated compounds are compounds comprising at least two (meth)acryl functions such as glycerol diacrylate, trimethylolpropane diacrylate, glycerol diacrylate, pentaerythritol triacrylate, ditrimethylolpropane triacrylate, dipentaerythritol pentaacrylate and their (poly)ethoxylated and/or (poly)propoxylated equivalents.

In embodiments of the present invention, n may preferably be from 1 to 50, more preferably from 1 to 31, still more preferably from 1 to 10, yet still more preferably from 2 to 5, and most preferably from 3 to 5 in order to provide sufficiently high integration in a (meth)acrylate network.

In embodiments of the present invention, m may preferably be from 1 to 50, more preferably from 1 to 31, still more preferably from 1 to 10, yet still more preferably from 1 to 5.

In embodiments of the present invention, x may preferably be from 0 to 50, more preferably from 0 to 31, still more preferably from 0 to 10, yet still more preferably from 0 to 5.

In embodiments of the present invention, p may preferably be from 0 to 30, more preferably from 0 to 5, still more preferably it is 0.

For instance, n and m may be independently from 1 to 31, preferably from 2 to 5, and x and p may be independently from 0 to 30, preferably from 0 to 5.

In embodiments of the present invention, n+m+x+p may be from 2 to 400, preferably from 2 to 200, more preferably from 2 to 100 still more preferably from 2 to 50, still more preferably from 2 to 32 and most preferably from 2 to 15.

For instance, n may be from 1 to 31, m may be from 1 to 31, x may be from 0 to 30, and p may be from 0 to 30 while n+m+x+p may be from 2 to 32. This last embodiment keeps the molecular weight relatively low which is advantageous to keep the viscosity relatively low.

In embodiments of the present invention, the compound may be a liquid at 25° C. and 1 atm. This is advantageous as it permits a greater solubility in an ink, coating or adhesive composition.

In a second aspect, the present invention relates to a compound obtained (or obtainable) by reaction of one or more amines of the general formula NHR$^6$R$^7$ with a benzophenone derivative of the following general formula (IX)

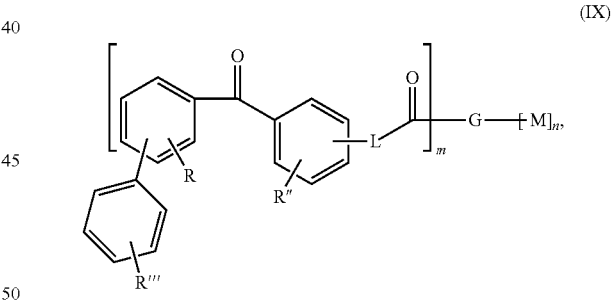

(IX)

wherein
R$^6$ and R$^7$ either:
  together with the N to which they are attached form a 5-6 membered saturated or aromatic ring optionally fused with a phenyl, said 5-6 membered ring containing one or more carbon atoms, from one to three nitrogen atom(s) and up to two oxygen atoms, or
  are independently selected from the group consisting of:
  H,
  $C_{1-30}$ alkyl,
  $C_{2-30}$ alkenyl, and
  5-6 membered saturated or aromatic ring containing one or more carbon atoms, up to three nitrogen atoms and up to two oxygen atoms, said ring being optionally substituted by a $C_{1-30}$ alkyl or by a $C_{1-30}$ alkyloxy or by a hydroxyl or by a $C_{1-6}$ acyloxy or fused with a phenyl, wherein each of said $C_{1-30}$ alkyl and $C_{2-30}$ alkenyl (as $R^1$ or $R^2$ group or as a substituent on a $R^1$ or $R^2$ group being a 5-6 membered saturated or aromatic ring) are independently optionally substituted with one or more substituents independently selected from:
   a 5-6 membered saturated or aromatic ring containing one or more carbon atoms, up to three nitrogen atoms and up to two oxygen atoms,
   a hydroxyl group,
   a $C_{1-10}$ alkoxy group, and
   an amine of formula —$NR^3R^4$, wherein $R^3$ and $R^4$ are independently selected from the group consisting of H and $C_{1-8}$ alkyl,
R, R", R''', L, M, as well as their connectivity are as defined in any embodiment of the first aspect,
m and n are as defined in any embodiment of the first aspect,
G is linker comprising a number p' of unreacted hydroxyl groups, and
p' is from 0 to 200.

Although some of the compounds of this other aspect are already covered by the first aspect of the present invention and are described in a Markush formula (I) (the case when $NHR^6R^7$ is a secondary amine with neither $R^6$ nor $R^7$ being a hydrogen atom) and the case when $NHR^6R^7$ is a primary amine with $R^6$ or $R^7$ being bulky (e.g. having the carbon in alpha of the nitrogen bonded to at least two carbon atoms), other compounds obtainable by reaction of one or more amines of the general formula $NHR^6R^7$ with a benzophenone derivative of the general formula (IX) cannot be described in a general Markush formula. This is the case when $NHR^6R^7$ is a primary amine (except for bulky amines as described above) with either $R^6$ or $R^7$ being a hydrogen atom. In this case, the product obtained by the addition of $NHR^6R^7$ on a (meth)acrylate group of the benzophenone derivative of the general formula (IX) is, due to the remaining active hydrogen on the amine, still prone to react with a second (meth)acrylate group (e.g. belonging to a second benzophenone derivative of the general formula (IX)). This starts a chain reaction that can lead to the formation of oligomers of complex structures and to a structure distribution. The resulting product is nevertheless useful as a photo-reactive binder and possesses the same advantages as provided by the compounds of the first aspect of the present invention.

Examples of useful secondary amines $NHR^6R^7$ may be amines of formula $NHR^1R^2$ as described in the first aspect of the present invention. Examples of useful primary amines of formula $NHR^6R^7$ wherein either $R^6$ or $R^7$ is a hydrogen atom are: methylamine, ethylamine, propylamine, butylamine, Sec-butylamine, ter-butylamine, amylamine(pentylamine), hexylamine, 2-ethylhexylamine, cyclohexylamine, octylamine, ter-octylamine, 3-morpholinopropylamine, dodecylamine, fatty amines (such as cocoamine), ethoxylated fatty amines, monoethanolamine(2-aminoethanol), 2-methoxyethylamine, 2-hydroxypropylamine, and mixtures thereof.

Especially preferred primary amines are monoethanolamine(2-aminoethanol), 2-ethylhexylamine, octylamine and cyclohexylamine, and mixtures thereof.

Examples of fatty amines are octyl amine, 2-ethylhexylamine, lauryl amine, stearyl amine, oleyl amine, tallowamine, cetylamine, N-tetradecylamine, cocoamine, di-cocoamine, hydrogenated tallowamine, alkyl($C_{16}$ and $C_{18}$-unsaturated) amine, alkyl($C_{14-18}$) amine, alkyl($C_{16-22}$) amine, alkyl($C_{8-18}$ and $C_{18}$-unsaturated) amine, alkyl($C_{12-18}$) amine, di(hydrogenated tallow)amine, dicocoalkyl amine, dialkyl($C_{14-18}$) amine, dialkyl($C_{12-18}$) amine, dialkyl($C_{16-22}$) amine, N-tridecyltridecanamine, N-methylstearylamine, distearyl amine, dialkyl($C_{8-20}$) amine, N-octadecylbenzylamine, N-isopropyloctadecylamine, and N-hexadecyloctadecylamine, and mixtures thereof.

Preferred fatty amines are cocoamine, di-cocoamine, octylamine, dodecylamine and 2-ethylhexylamine, and mixtures thereof.

G may be a residue of a polyhydroxy compound as defined in any embodiments of the first aspect of the present invention.

In embodiments, G may have at most 200 hydroxyl groups, preferably at most 150 hydroxyl groups, more preferably at most 100 hydroxyl groups, still more preferably at most 50 hydroxyl group, still more preferably at most 32 hydroxyl groups, still more preferably at most 16 hydroxyl groups, yet still more preferably at most 12 hydroxyl groups and most preferably at most 6 hydroxyl groups.

In embodiments, the equivalent weight of acrylic double bonds of the compound according to the first aspect of the present invention may be 1 meq/g or more, preferably 2 meq/g or more, most preferably 3 meq/g or more.

In embodiments, the equivalent weight of acrylic double bonds of the compound according to the first aspect of the present invention may be 11 meq/g or less, preferably 8 meq/g or less, most preferably 5 meq/g or less.

In another aspect, the present invention relates to a blend comprising an amine synergist, such as an amino(meth) acrylate, typically an aminoacrylate, and a compound according to any embodiment of the first aspect or of the second aspect of the present invention. In this aspect, x is preferably 0 since an amine synergist is already provided in the blend. Yet, of course x can also be different from 0 if one wishes to raise the nitrogen content. The amine synergist used in the blend can also be one or more of the polymeric tertiary amines described above. Possibly a mix of at least one amino(meth)acrylate and at least one of these polymeric tertiary amines is being used. Other types of co-initiators that may be used in addition to or instead of the above include: aliphatic tertiary amines, aromatic amines and/or thiols.

In a further aspect, the present invention relates to a composition comprising the compound or blend according to any embodiment of the present invention. The composition can for instance be an ink, a coating composition (e.g. a varnish) or an adhesive. The compounds of the first and second aspect of the present invention are particularly useful in an ink for printing food packaging or in a varnish for coating food packaging. The compounds of the present invention having the ability to integrate covalently a (meth) acrylate network upon curing, (meth)acrylate based compositions comprising said compound are particularly safe to use for food packaging where migration must be avoided.

In embodiments, the compound of the present invention may be present in an amount of 0.1 wt % or more, preferably 5 wt % or more, and most preferably 10 wt % or more in the composition (e.g. ink or varnish).

In embodiments, the compound of the present invention may be present in an amount of 90 wt % or less, preferably 50 wt % or less and most preferably 35 wt % or less in the composition (e.g. ink or varnish).

In yet a further aspect, the present invention relates to a substrate coated or printed with a coating as described above. The coating may be cured or uncured but will typically be cured. Such substrates have the advantage to leach no or negligible amounts of initiator (and amine synergist if x is at least 1). Particularly advantageous are food packaging printed with an ink or coated with a varnish as described above. Food packaging must meet strict chemical migration requirements that the inks/varnishes as described above help to meet. Furthermore, inks/varnishes for food packaging preferably have good flow properties and high UV reactivity. Two features that the inks/varnishes as described above also help to meet. This is especially true when the compound of the first or second aspect present in said coatings is a liquid.

In yet a further aspect, the present invention relates to a process for the synthesis of a compound according to the first or second aspect of the present invention.

The synthesis may proceed by the reaction of 1) a phenyl substituted benzophenone derivative bearing on its benzophenone moiety a reactive group capable to react with a hydroxyl group to form e.g. an ester with 2) a linker comprising from 2 to 400 hydroxyl groups, 3) a (meth)acrylating compound of a second type, and optionally 4) a primary or secondary amine of general formula $NHR^6R^7$ or a tertiary amine $Q'-NR^1R^2$ wherein $R^6$, $R^7$, $R^1$ and $R^2$ are as defined above and wherein Q' comprises a reactive group capable to react with a hydroxyl group to form e.g. an ester. Combinations of different amines (e.g. some of formula $NHR^6R^7$ and some of formula $Q'-NR^1R^2$) can also be used.

The (meth)acrylating compound of a second type is a compound comprising at least one (meth)acrylate group and at least one reactive group capable to react with an hydroxyl group. Examples of such reactive group capable to react with a hydroxyl group are carboxylic acid, activated carboxylic acid, carboxylic acid esters, or isocyanate groups. An example of (meth)acrylating compound is (meth)acrylic acid itself.

A (meth)acrylating compound of a second type can be obtained by the reaction of a (meth)acrylating compound of a first type and a linker comprising at least two reactive groups capable to react with an hydroxyl. Examples are polyisocyanates and polycarboxylic acids. Examples of suitable diisocyanate and triisocyanate are:

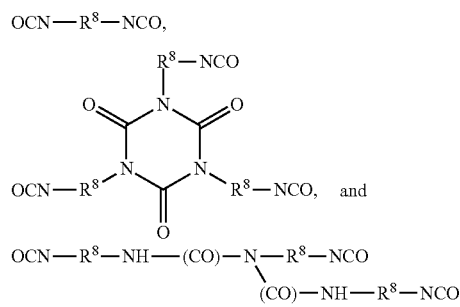

wherein $R^8$ is as described above. An example of polycarboxylic acid is $HOOCR^8COOH$, activated versions thereof or transesterifiable ester thereof wherein $R^8$ is as described above.

In an alternative embodiment, the synthesis may proceed by the reaction of 1) a phenyl substituted benzophenone derivative bearing on its benzophenone moiety a reactive group capable to react with a hydroxyl group to form e.g. an ester with 2) a linker comprising from 2 to 400 hydroxyl groups, 3) a linker comprising at least two reactive groups capable to react with an hydroxyl, 4) a (meth)acrylating compound of a first type, and optionally 5) a primary or secondary amine of general formula $NHR^6R^7$ or a tertiary amine $Q'-NR^1R^2$. Combinations of different amines (e.g. some of formula $NHR^6R^7$ and some of formula $Q'-NR^1R^2$) can also be used.

The linker comprising from 2 to 400 hydroxyl groups may be a polyhydroxy compound as defined in any embodiment of the first aspect of the present invention.

Q' may for instance comprise a carboxylic acid, an activated carboxylic acid or a transesterifiable ester group.

Q' may for instance be selected from the list consisting of the following groups: a $C_{1-8}$ straight or branched alkyl, a $C_{4-10}$ cyclic alkyl optionally substituted with a $C_{1-4}$ straight or branched alkyl, and a phenyl group optionally substituted with a $C_{1-4}$ straight or branched alkyl, wherein said groups are substituted with one or more carboxylic acid, activated carboxylic acid or transesterifiable carboxylic ester groups.

This permits the carboxylic acid or ester group of Q' to form an ester with a hydroxyl of the linker G. For instance, Q' may be $HO-C(O)(CH_2)_2-$ or may be $CH_3-O-C(O)-C_6H_6-$ or may be $HO-C(O)C_6H_6-$.

The phenyl substituted benzophenone derivative may have the following general formula (X):

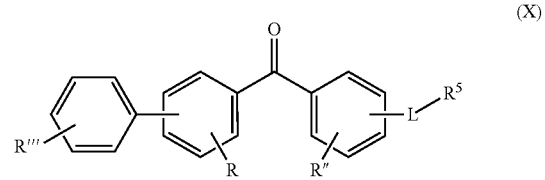

wherein L, R, R" and R''' as well as their connectivity are as defined above for the compound of the first aspect of the present invention and wherein $R^5$ is a reactive group capable to react with a hydroxyl group to form e.g. an ester. This group can for instance be a carboxylic acid group or a modified carboxylic acid group capable to react with a hydroxyl group to form an ester. Examples of modified carboxylic groups are methyl carboxylate and activated carboxylic acid groups such as an acyl halide group (e.g. an acyl chloride or acyl bromide group) or an anhydride group. The connectivity of the phenyl bearing the R''' group can be as defined above for the compound of the first aspect of the present invention.

The phenyl-substituted benzophenone derivative can be for instance 2-(4-phenylbenzoyl)benzoic acid.

The preparation of 2-(4-phenylbenzoyl)benzoic acid is for example described in U.S. Pat. No. 1,814,145 from phthalic anhydride and biphenyl.

The linker comprising reactive groups capable to react with a carboxylic acid group or with an activated carboxylic acid group to form an ester may be a polyhydroxy compound as defined above or a polyhydroxy compound which hydroxyl groups have been modified into other reactive groups capable to react with a carboxylic acid or an activated carboxylic acid to form an ester (as also defined above).

In an embodiment, the phenyl substituted benzophenone derivative may be first reacted with said linker, and in a second step with said (meth)acrylating compound of a second type.

Alternatively, the phenyl substituted benzophenone derivative and the (meth)acrylating compound of the second type can be reacted together with the linker.

Alternatively, the (meth)acrylating compound of the second type may be first reacted with said linker, and in a second step the reaction product of the first step is then further reacted with a phenyl substituted benzophenone derivative as described above.

In embodiments, the phenyl-substituted benzophenone derivative may be reacted with the reactive groups (e.g. hydroxyls groups) of the linker (e.g. polyhydroxy compound) by an esterification reaction with equivalent ratios of 0.05:1 or more, preferably of 0.1:1 or more and most preferably of 0.2:1 or more.

In embodiments, the phenyl-substituted benzophenone derivative may be reacted with the reactive groups (e.g. hydroxyls groups) of the linker (polyhydroxy compound) by an esterification reaction with equivalent ratios of 0.95:1 or less, preferably of 0.75:1 or less and most preferably of 0.5:1 or less.

After reaction between the phenyl-substituted benzophenone derivative and the linker, residual reactive groups on the linker (e.g. hydroxyl groups) may be further reacted partially or totally with a (meth)acrylating compound of the second type.

In an embodiment, the process may further comprise reacting the reaction product of the linker, the phenyl-substituted benzophenone derivative and a (meth)acrylating compound with at least one amine of general formula $NHR^6R^7$ or $Q'-NR^1R^2$, thereby obtaining an amino photo-reactive binder. Combinations of different amines (e.g. some of formula $NHR^6R^7$ and some of formula $Q'-NR^1R^2$) can also be used.

When at least one primary and/or at least one secondary amine is reacted, it is preferably reacted after that the phenyl-substituted benzophenone, the (meth)acrylating compound of the second type and the linker have been reacted together.

In an embodiment of the present invention, the amino photo-reactive binder may be obtained by the reaction of at least one primary and/or at least one secondary amine with part of the (meth)acrylic unsaturations of the photo-reactive binder. It is advantageous to keep at least one (meth)acrylic unsaturation unreacted in order to insure that the obtained amino photo-reactive binder has at least one (meth)acrylic unsaturation for future integration in a (meth)acrylate network.

In an embodiment of the present invention, the amino photo-reactive binder may be prepared by performing an Aza-Michael addition of at least one primary and/or at least one secondary amine onto a (meth)acrylate function of the photo-reactive binders. An example of amino photo-reactive binder preparation is shown below:

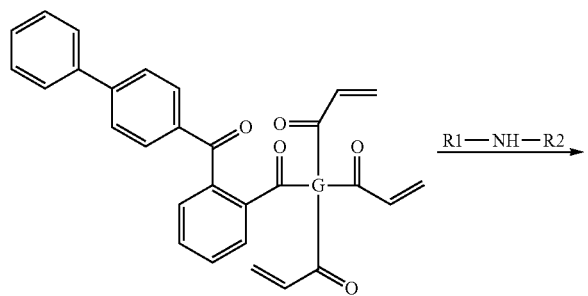

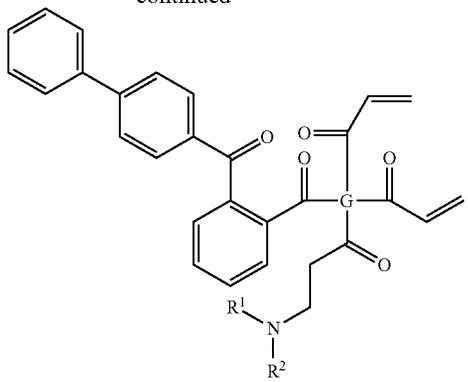

Amines used to prepare "amino photo-reactive binders" of the present invention are generally selected from primary amines ($R^1$—$NH_2$) and/or secondary amines ($R^1$—NH—$R^2$) as described in the first and second aspect of the present invention.

In an embodiment, the amino photo-reactive binder may be prepared by an addition reaction of at least one primary and/or at least one secondary amine to (meth)acrylic double bonds with an equivalent ratio amine:(meth)acrylic double bonds of 0.05:1 or more, preferably 0.1:1 or more and most preferably 0.2:1 or more.

In an embodiment, the amino photo-reactive binder may be prepared by an addition reaction of at least one primary and/or at least one secondary amine to (meth)acrylic double bonds with an equivalent ratio amine:(meth)acrylic double bonds of 0.95:1 or less, preferably 0.75:1 or less and most preferably 0.5:1 or less.

In an embodiment, the amino photo-reactive binder may be prepared by an esterification or transesterification reaction between a) a tertiary amine bearing reactive groups capable to react with an hydroxyl to form e.g. an ester (e.g. carboxylic acid groups or the corresponding esters), and b) hydroxyl groups on the linker G.

Examples of tertiary amines that can be used are polymeric tertiary amines. By "polymeric" is meant that the number average molecular weight (Mn) of the polymeric tertiary amine is preferably of 400 g/mol or more, more preferably of 500 g/mol or more and most preferably of 600 g/mol or more. Typically the molecular weight of these compounds is at most 5.000 g/mol, more preferably at most 3.000 g/mol and most preferably at most 2.000 g/mol.

An example of suitable polymeric tertiary amines in this category: dialkyl aminobenzoate esters and more in particular dimethylaminobenzoate esters as described e.g. in U.S. Pat. No. 5,905,164. Both monoamines and diamines can be used, possibly a mixture of both.

An example of a suitable diamine compound in this category is polyethyleneglycol bis(p-dimethyl aminobenzoate) as disclosed in U.S. Pat. No. 5,905,164

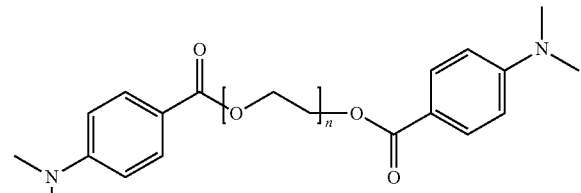

These compounds typically exist in a mixture as described in U.S. Pat. No. 5,905,164 p10, with n typically in the range of from 2 to 110, more preferably from 4 to 61, most preferably from 7 to 40.

Another example of a suitable diamine compound in this category is polytetrahydrofurane bis(p-dimethyl aminobenzoate)

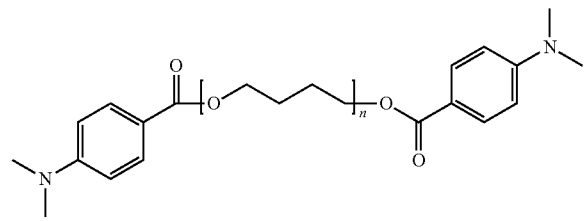

with n typically in the range of from 2 to 65, more preferably from 3 to 40, most preferably from 4 to 25.

An example of a suitable monoamine compound in this category is 4-N,N'-dimethylaminobenzoyl polyethyleneglycol monomethylether as disclosed in U.S. Pat. No. 5,905,164

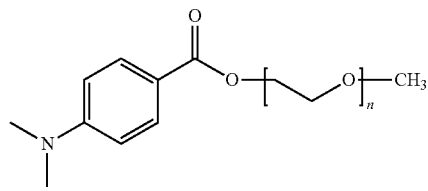

with n typically in the range of from 2 to 110, more preferably from 4 to 61, most preferably from 7 to 40.

Particularly preferred compounds in this category are Omnipol ASA from IGM (a Poly(ethyleneglycol) bis(p-dimethylamino benzoate) with number average molecular weight 488-532 g/mol), ESACURE™ A198 from Lamberti & Speedcure 7040 from Lambson (polymeric (mix 4+2) amine with number average molecular weight 1060 g/mol).

In an embodiment, the amine(s) may be added in an amount such that the reaction product has a nitrogen content of 0.1% wt or more, preferably 0.2% wt or more and most preferably 0.3% wt or more.

In an embodiment, the amine(s) may be added in an amount such that the reaction product has a nitrogen content of 10% wt or less, preferably 5% wt or less and most preferably 3% wt or less.

In an embodiment, the residual (meth)acrylic content in the amine photo-reactive binder (e.g. after reaction of the amine(s) with the photo-reactive binder) is 0.5 meq/g or more, preferably 1 meq/g or more, most preferably 2 meq/g or more.

In an embodiment, the residual (meth)acrylic content in the amine photo-reactive binder (e.g. after reaction of the amine(s) with the photo-reactive binder) is 10 meq/g or less, preferably 8 meq/g or less, most preferably 5 meq/g or less.

In embodiments where the primary or secondary amine is an aromatic amine, an appropriate catalyst is preferably used to promote the Aza-Michael addition. For instance, the catalyst may be selected from Brønsted or Lewis acids or bases, yttrium trinitrate hexahydrate ($Y(NO_3)3.6H_2O$), ionic liquids, clays and other catalysts described in Tetrahedron Letters 47 (2006)7723-7726 and Catalysis Communications 9 (2008) 1189-1195 or glacial acetic acid as described in WO 2011/117591 A2 (Sun Chemical). This is advantageous since it permits to obtain good yield despite the lower nucleophilicity of aromatic amines when compared to alkyl or alkenyl amines.

Yet another aspect of the invention concerns products obtainable by a process according to the invention.

DESCRIPTION OF ILLUSTRATIVE EMBODIMENTS

The present invention will be described with respect to particular embodiments but the invention is not limited thereto.

EXAMPLE 1

General Procedure for the Synthesis of a Compound PI1 (of General Formula XII) and for Comparative Compounds PI2 and PI3

To a 1 liter double jacketed reactor vessel connected to an oil bath and equipped with a stirrer, was added 100 g of polyhydroxy compound 4631 (polyhydroxy compound commercially available from Perstorp); "a" g of acrylic acid; "b" g of paratoluenesulfonic acid; "c" g of carboxy substituted benzophenone "d"; 1000 ppm of a phosphite type inhibitor; 600 ppm of a hydroquinone type inhibitor; 1250 ppm of a cupper type inhibitor and 116 g of toluene. The reaction mixture was stirred and heated under reflux until no more water was distilled. The reaction mixture was cooled down to 60° C. and diluted with 39 g of toluene. The reaction mixture was washed 3 times with an aqueous solution (15 wt %) of sodium sulphate. Water was then removed by azeotropic distillation under reduced pressure. Once no more water distilled, the organic mixture was filtered at 50° C. and toluene was removed by distillation under reduced pressure. The table below gives the values for parameters "a", "b", "c" and "d".

| | PI 1 (ex. 1.1) | PI 2 (comp. ex. 1.2) | PI 3 (comp. ex. 1.3) |
|---|---|---|---|
| "a" | 86 | 86 | 66 |
| "b" | 5 | 5 | 4 |
| "c" | 85 | 89 | 73 |
| "d" | 2-(4-Phenyl-benzoyl)benzoic acid | 2-(4-Phenoxy-benzoyl)benzoic acid | 2-(4-chloro-benzoyl)benzoic acid |

Precursors:

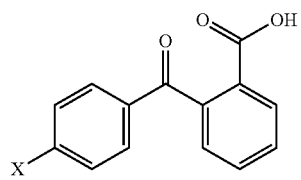

2-(4-Phenylbenzoyl)benzoic acid precursor (example 1.1): X=Phenyl
2-(4-Phenoxybenzoyl)benzoic acid precursor (comparative example 1.2): X=Phenoxy
2-(4-chlorobenzoyl)benzoic acid precursor (comparative example 1.3): X=Cl

EXAMPLE 2

Formulation of Overprint Varnishes (OPV)

Overprint varnishes formulations were prepared by mixing the photo-reactive binder (PI1/PI2/PI3) with monomer EBECRYL LEO™ 10501 and amino synergist Ebecryl LEO™ 10552 (available from Cytec). Cured films (4 μm layer) were prepared using a bar coater and cured by UV (120 W/cm).

| Ex | Photo-reactive binder wt % | Monomer wt % | Amine synergist wt % | Viscosity of OPV formulation mPa · s @25° C. |
|---|---|---|---|---|
| OPV3 (comp.) | 15% PI 3 | 25 | 60 | 340 |
| OPV1 | 15% PI 1 | 25 | 60 | 440 |
| OPV2 (comp) | 15% PI 2 | 25 | 60 | 460 |

EXAMPLE 3

Evaluation of Cure Performance in OPVs Prepared in Example 2

| Cured formulation under nitrogen atmosphere at 4 μm | Cure speed by "Graphite test" (surface cure) Under nitrogen m/min | Cure speed by "Graphite test" (surface cure) Under air m/min | Acetone double rubs (full cure assessment) (after 1 and 5 passes at 60 m/min) Nitrogen 1× | 5× | Air 1× | 5× |
|---|---|---|---|---|---|---|
| OPV 3 (comp) | 30 | 10 | 30 | 80 | 1 | 60 |
| OPV 1 | >80 | 30 | 15 | 60 | 4 | 60 |
| OPV 2 (comp) | 50 | 10 | 8 | 40 | 0 | 12 |

UV reactivity was assessed by the "graphite test" (the higher the number, the higher the surface reactivity) and acetone double rubs test (the higher the number, the higher the deep curing reactivity).

Graphite Test:

This test is performed by placing some graphite on the coated surface, followed by rubbing said surface with a piece of cotton. If no black stain remain on the surface, the surface is considered cured.

"10 m/min" means that curing at 10 m/min was necessary to pass the graphite test.

Acetone Double Rubs Test:

The rubs are made with a piece of cotton rag saturated with acetone; one double rub is equal to a forward and backward stroke on the coated surface. The reported number is the number of double rubs required to break through the coating. "60" means that 60 doubles rubs are necessary to break through the coating.

Copolymerizable formulation (OPV 1) based on photo-reactive binder based on 2-(4-phenylbenzoyl)benzoic acid precursor (PI 1) according to an embodiment of the present invention shows significantly better surface cure (in air and nitrogen atmosphere) than formulations OPV 3 (comp) and OPV 2 (comp) based on 2-(4-chlorobenzoyl)benzoic acid precursor (PI3) and based on 2-(4-phenoxybenzoyl)benzoic acid precursor (PI2).

The full cure reactivity assessed by the number of acetone double rubs illustrates that copolymerizable formulation (OPV 1) based on a photo-reactive binder according to the present invention PI 1 has full cure reactivity in the same order of magnitude as formulations OPV 3 and significantly higher than OPV 2 (in nitrogen and air atmosphere).

At same UV dose, the higher photo-reactivity of PI 1 over PI 2 and PI 3 is expected to result in a significantly lower migration level of a cured film based on OPV 1 than of a cured films based on OPV 3 (comp) and OPV 2 (comp).

These tests demonstrate the advantage of a benzophenone substituted with a phenyl group compared to other benzophenone derivatives such as those substituted with a chlorine or a phenoxy group.

EXAMPLE 4

Evaluation of the Photo-Reactivity of Flexo Inks (FI) According to an Embodiment of the Present Invention

| | FI 3 (comp) Wt % | FI 1 Wt % | FI 2 (comp) Wt % |
|---|---|---|---|
| Magenta pigment paste based on EBECRYL® 452 | 35 | 35 | 35 |
| photo-reactive binder PI 1 | | 26 | |

-continued

| | FI 3 (comp) Wt % | FI 1 Wt % | FI 2 (comp) Wt % |
|---|---|---|---|
| photo-reactive binder PI 2 | | | 29 |
| photo-reactive binder PI 3 | 30 | | |
| EBECRYL LEO ™ 10501 | 5 | 9 | 6 |
| EBECRYL LEO ™ 10551 | 30 | 30 | 30 |
| Halogen-free | no | yes | yes |
| Cure speed 120 W/cm (m/min) under air atmosphere | 20 | 20 | 10 |
| Cure speed 120 W/cm (m/min) under nitrogen atmosphere | >80 | >80 | 50 |

Copolymerizable formulation (FI 1) based on a photo-reactive binder according to an embodiment of the present invention PI 1 shows significantly better cure speed in air and nitrogen atmosphere than formulations FI 2 (comp) and similar cure speed as FI 3 (comp). Photo-reactive binder PI 1 has the advantage over PI 3 to be halogen-free whereas PI 3 contains chlorine. Halogen-free formulations are highly preferred for food-packaging applications.

At same UV dose, the significantly higher photo-reactivity of PI 1 over PI 2 is expected to result in a significantly lower migration level for the cured films made from FI 1 over the ones made from FI 2 (comp).

EXAMPLE 5

Preparation of a Compound PI4 According to an Embodiment of the Present Invention Wherein x=1: Reaction of a Primary or Secondary Amine with an Acrylated Carboxy Substituted Benzophenone Polyhydroxy Compound 1.65 g of diethylamine (secondary amine) was added to 20 g of the acrylated carboxy substituted benzophenone polyhydroxy compound (see example 1.1), homogenized and heated at 40° C. for 24 hours.

EXAMPLE 6

Evaluation of the Photoreactivity of the Compound PI4

|  | OPV 4 Wt % | OPV 5 Wt % |
|---|---|---|
| EBECRYL LEO ™ 10501 | 70 | 70 |
| PI 4 | 30 |  |
| PI 1 |  | 30 |
| Graphite test m/min under air 4 microns | 10 | <1 |
| ADR test 60 m/min (1x) under air 4 microns | 4 | 0 |
| ADR test 60 m/min (5x) under air 4 microns | 30 | 1 |

ADR: acetone double rubs

The photo reactivity of the formulation based on photoreactive binder PI 1 reacted with amine synergist 1 (diethylamine adduct) (PI 4) is significantly higher than the photo reactivity of a formulation based on the Photo-reactive binder without amine synergist (2-(4-Phenylbenzoyl)benzoic acid precursor PI 1) (OPV 5).

This shows that the amine synergist keeps its co-initiating role despite being covalently bound to the PI.

EXAMPLE 7

Evaluation of the Photoreactivity of the Compound PI 4 Compared with Commercially Available Polymeric Photoinitiators Omnipol BP is a di-functional benzophenone photoinitiator specifically designed for use in inks and coatings requiring low migration and low volatility. It is particularly suited to use, in combination with amine synergists, in non-pigmented coatings as an alternative to benzophenone. Its chemical structure is Di-ester of carboxymethoxy-benzophenone and polytetramethylene glycol 250; molecular weight 730; CAS 515136-48-8

Omnipol 910 is a kind of photoinitiator with high activity, good compatibility, low odor and migration, and with low fragments releasing after curing. It is specifically designed for use in inks and coatings requiring low migration and low volatiles. Its chemical structure is Polyethylene Glycol di(β-4[4-(2-dimethylamino-2-benzyl) butaonylphenyl]piperazine) propionate, molecular weight 1032; CAS 886463-10-1

The following formulations were prepared and their cure-speed was assessed by curing film at 1.5 g/m² under air using a UV lamp of 120 W/cm. Graphite test (m/min) gives the speed at which a stain free print is obtained; the higher the more reactive. The Total Energy dose (mJ/cm²) is the energy necessary to have a stain free print; the lower the more reactive.

|  | FI 4 (comp) | FI 5 | FI 6 (comp) | FI 7 | FI 8 (comp) | FI 9 | FI 10 (comp) | FI 11 |
|---|---|---|---|---|---|---|---|---|
| EBECRYL 452 | 26.5 | 26.5 | 18.9 | 18.9 | 19 | 19 |  |  |
| EBECRYL LEO 10601 |  |  |  |  |  |  | 10.8 | 10.8 |
| EBECRYL LEO 10501 |  |  |  |  |  |  | 13.5 | 13.5 |
| ADDITOL S 130 | 0.4 | 0.4 | 0.35 | 0.35 | 0.35 | 0.35 | 0.45 | 0.45 |
| Solspers 39000 (Lubrizol) | 0.8 | 0.8 | 1.75 | 1.75 | 1.3 | 1.3 | 2.25 | 2.25 |
| Solsperse 22000 (Lubrizol) | 0.3 | 0.3 |  |  |  |  |  |  |
| Solsperse 5000 (Lubrizol) |  |  |  |  | 0.35 | 0.35 |  |  |
| Yellow DGR (Clariant) | 12 | 12 |  |  |  |  |  |  |
| Magenta pigment 4 BY (SUN) |  |  | 14 | 14 |  |  |  |  |
| Cyan pigment GLO (Ciba-BASF) |  |  |  |  | 14 | 14 |  |  |
| Special Black 250 (Evonik) |  |  |  |  |  |  | 18 | 18 |
| EBECRYL 570 | 10 | 10 | 10 | 5 | 10 | 5 | 5 |  |
| EBECRYL LEO 10501 | 10 | 20 | 15 | 30 | 15 | 30 | 10 | 25 |
| EBECRYL LEO 10551 | 30 | — | 30 | — | 30 | — | 30 |  |
| Ominpol BP (IGM) | 5 |  | 5 |  | 5 |  | 5 |  |
| Omnipol 910 (IGM) | 5 |  | 5 |  | 5 |  | 5 |  |
| PI 4 |  | 30 |  | 30 |  | 30 |  | 30 |
|  | 100 | 100 | 100 | 100 | 100 | 100 | 100 | 100 |
|  | Cure speed-under air-1.5 g/m² film-120 W/cm | | | | | | | |
| Graphite test (m/min) | 10 | 30 | 20 | 40 | 20 | 45 | 20 | 50 |

-continued

|  | FI 4 (comp) | FI 5 | FI 6 (comp) | FI 7 | FI 8 (comp) | FI 9 | FI 10 (comp) | FI 11 |
|---|---|---|---|---|---|---|---|---|
| Total Energy dose (mJ/cm$^2$) | 700 | 260 | 400 | 180 | 400 | 160 | 400 | 140 |

The photoreactivity of compound PI 4 was compared with a mixture of the two Omnipol BP and 910 polymeric photoinitiator in flexo inks (4 process colors). Overall, an addition of 30 wt % of compound of PI 4 leads to higher reactivity than comparative examples using commercial photoinitiators instead.

EXAMPLE 8

Preparation of a Compound PI 5 According to an Embodiment of the Present Invention: Reaction of a Primary (Octylamine) and Secondary Amine (Dibutylamine) with an Acrylated Carboxy Substituted Benzophenone Polyhydroxy to compound PI1

45.8 g of dibutylamine (secondary amine) and 30.5 g of octylamine (primary amine) were added to 750 g of the acrylated carboxy substituted benzophenone polyhydroxy compound (PI 1, see example 1.1), homogenized and heated at 40° C. for 24 hours. The nitrogen content is 1 wt %.

EXAMPLE 9

Examples of Formulations Suited for Lithographic Ink Applications

The following examples FI 12-13-14 are examples of formulations based on photoreactive binder PI1 blended with polymeric amines. Examples FI 15 are examples of formulations based on photoreactive binder PI 5 (PI1 reacted with dibutylamine and octylamine). These formulations are suited for litho inks applications (limited water uptake and good UV reactivity).
Formulations Offset Black Inks

|  | FI 12 | FI 13 | FI 14 | FI 15 |
|---|---|---|---|---|
| EBECRYL 570 | 45 | 40 | 45 | 40 |
| EBECRYL 40 | 4 | 9 | 4 | 9 |
| Solsperse 39000 | 2 | 2 | 2 | 2 |
| Additol S 130 | 1 | 1 | 1 | 1 |
| Black Pigment Special black 250 (Evonik) | 18 | 18 | 18 | 18 |
| PI 1 | 25 | 25 | 25 |  |
| PI 5 |  |  |  | 30 |
| Omnipol ASA | 5 |  |  |  |
| ESACURE ™ A 198 |  | 5 |  |  |
| Speedcure 7040 |  |  | 5 |  |
| Total | 100 | 100 | 100 | 100 |
| Visco 2.5 1/s at 25° C. | 43 | 74.4 | 32 | 46.5 |
| Visco 100 1/s | 28.3 | 36.8 | 29.3 | 34 |
| SI 2.5 - 100 | 1.5 | 2 | 1.1 | 1.4 |
| Cure speed 120 W/cm (m/min) Graphite test | 30 | 35 | 25 | 35 |
| Water uptake (emulsion point in %) | 58 | 33 | 38 | 32 |

Water take up test on hydroscope (Testprint): the device consists of three rollers: a small rubber roller—measures the tack of the ink film- and two larger temperature controlled metal rollers. Above the two metal rollers there is a space (ink reservoir) where 10 g of ink is inserted. The sides of the ink bath have been sealed, so that all ink and water are enclosed therein. Fountain solution is dripped into the ink at a speed of 1.3 ml/min, using an accurate pumping system, located at two points above the ink bath. Ink and fountain solution are jointly forced through the opening between the rollers, so that they undergo a joint shear stress. When an excess of water starts to appear on the ink surface, the ink is "saturated" with water, indicating the emulsion point (expressed in %).

The invention claimed is:
1. A process for the synthesis of a compound having the following formula (I),

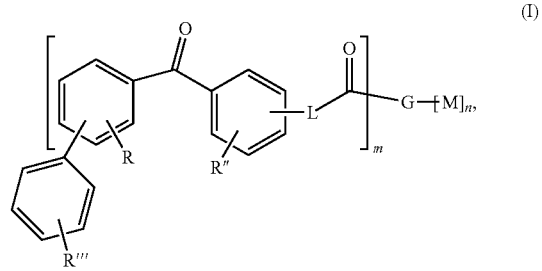

comprising reacting:
  a) a benzophenone derivative of the following general formula

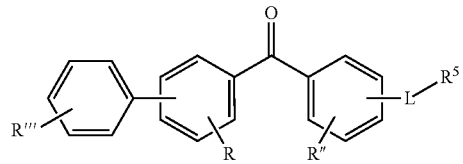

b) a linker comprising from 4 to 300 hydroxyl groups, and
  c1) a (meth)acrylating compound comprising at least one (meth)acrylate group and at least one reactive group capable to react with an hydroxyl group, or
  c2) a linker comprising at least two reactive groups capable to react with a hydroxyl, then a (meth)acrylating compound comprising at least one (meth)acrylate group and at least one hydroxyl,
  wherein in the formulas:
  L is a linker,
  $R^5$ is a reactive group capable to react with a hydroxyl group to form an ester,
  R, R" and R'" are independently selected from the group consisting of H, $C_{1-8}$ alkyl, $C_{1-10}$ alkoxy and halogen,
  m is from 1 to 100,
  n is from 1 to 100, G is a linker comprising a number p of unreacted hydroxyl groups comprised between 0 and 100, and is a residue of a polyhydroxy compound having at least 4 hydroxyl groups, and M is a group comprising a number z of (meth)acrylate groups equal to at least one.

2. The process according to claim 1, wherein the compound has the following formula (II),

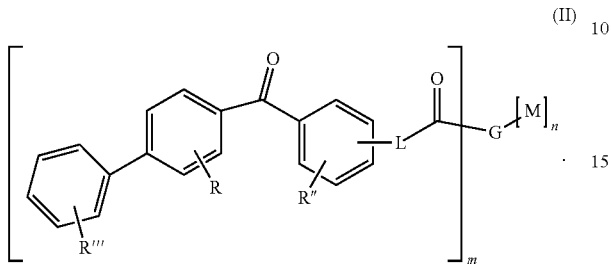
(II)

3. The process according to claim 2, wherein the compound has the following formula (IV),

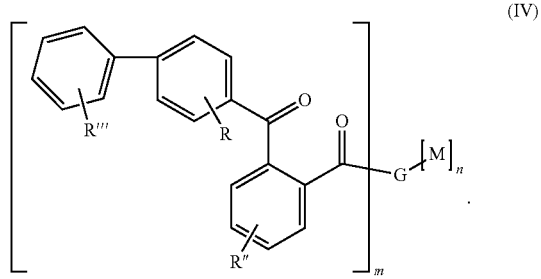
(IV)

4. The process according to claim 3, wherein the compound has the following formula (VI),

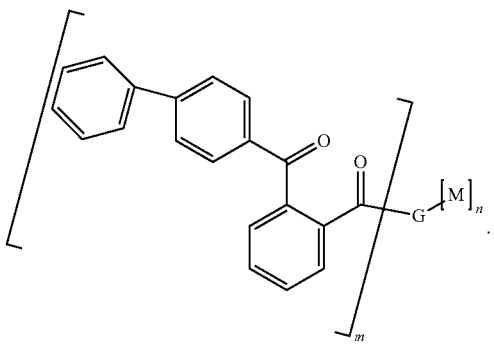
(VI)

5. The process according to claim 1, wherein
the linker b) comprises from 4 to 92 hydroxyl groups,
n and m are independently from 1 to 31, and
p is from 0 to 30.

6. The process according to claim 5, wherein the linker b) comprises from 4 to 40 hydroxyl groups and n and m are independently from 1 to 5.

7. The process according to claim 5, wherein the linker b) comprises from 4 to 66 hydroxyl groups and p is from 0 to 4.

8. The process according to claim 1, wherein n is from 2 to 100.

9. The process according to claim 8, wherein the linker b) comprises from 4 to 205 hydroxyl groups and n is from 2 to 5.

* * * * *